United States Patent [19]

Costantini et al.

[11] Patent Number: 5,097,078
[45] Date of Patent: Mar. 17, 1992

[54] CATALYTIC HYDROXYLATION OF PHENOLS/PHENOL ETHERS

[75] Inventors: Michel Costantini; Dominique Laucher, both of Lyons, France

[73] Assignee: Rhone-Poulenc Chimie, Courbevoie, France

[21] Appl. No.: 549,148

[22] Filed: Jul. 6, 1990

[30] Foreign Application Priority Data

Jul. 11, 1989 [FR] France .................. 89 09672

[51] Int. Cl.$^5$ .................................. C07C 37/60
[52] U.S. Cl. .................... 568/771; 568/651; 568/652; 568/653; 568/741; 568/803
[58] Field of Search .......... 568/771, 741, 803, 650, 568/651, 652, 653

[56] References Cited

U.S. PATENT DOCUMENTS

| | | | |
|---|---|---|---|
| 3,836,591 | 9/1974 | Maggino | 568/771 |
| 3,849,502 | 11/1974 | Bourdin et al. | 568/771 |
| 3,914,324 | 10/1975 | Maggino | 568/771 |
| 3,953,527 | 4/1976 | Bost et al. | 568/771 |
| 4,045,496 | 8/1977 | Seifert et al. | 568/771 |
| 4,053,523 | 10/1977 | Seifert et al. | 568/771 |
| 4,078,006 | 3/1978 | Umemura et al. | 568/771 |
| 4,208,536 | 6/1980 | Costantini et al. | 568/771 |
| 4,223,165 | 9/1980 | Jouffret | 568/771 |
| 4,301,307 | 11/1981 | Jouffret | 568/771 |

FOREIGN PATENT DOCUMENTS

| | | | |
|---|---|---|---|
| 2064497 | 7/1971 | Fed. Rep. of Germany | 568/803 |
| 2138735 | 3/1973 | Fed. Rep. of Germany | 568/771 |

OTHER PUBLICATIONS

"Methoden der Organischen Chemie", Eugen Müller, 1976.

Primary Examiner—Werren B. Lone
Attorney, Agent, or Firm—Burns, Doane, Swecker & Mathis

[57] ABSTRACT

The phenols and phenol ethers are hydroxylated by reacting such phenols/phenol ethers with hydrogen peroxide, in the presence of (a) a catalytically effective amount of an alkali metal or alkaline earth metal salt of at least one protonic acid having a pKa in water of less than −0.1, and (b) an effective amount of at least one phosphorus oxyacid.

23 Claims, No Drawings

CATALYTIC HYDROXYLATION OF PHENOLS/PHENOL ETHERS

BACKGROUND OF THE INVENTION

1. Field of the Invention

The present invention relates to the hydroxylation of phenols and phenol ethers, and, more especially, to the hydroxylation of phenols and phenol ethers by reaction with hydrogen peroxide.

2. Description of the Prior Art

French Patent No. 69/45,467, published under U.S. Pat. No. 2,071,464, describes a process for the hydroxylation of phenols and phenol ethers using hydrogen peroxide, in the presence of a strong acid catalyst. Exemplary of such strong acids are sulfuric acid, paratoluenesulfonic acid and perchloric acid.

The process of this '467 patent is very significant commercially. Nonetheless, this art has long sought an alternative catalytic process wherein the catalyst would be less corrosive for the apparatus employed.

Thus, published French Patent Application FR-2,489,816 specifies the use of silicalites of various metals for such purpose.

And published European Patent Application EP-A-0,299,893 describes the use of bridged clays.

Although these processes which employ heterogeneous catalysis would appear to be desirable alternatives, it has transpired that, on the one hand, industrial-scale problems such as the recycling of the catalyst still exist and that, on the other, the efficacy thereof is not fully on the level of the process employing a strong acid catalyst.

SUMMARY OF THE INVENTION

Accordingly, a major object of the present invention is the provision of an improved catalytic process for the hydroxylation of phenols and phenol ethers that permits yields as high as those of the strong acid process to be attained, while at the same time significantly reducing the risk of processing apparatus corrosion.

Briefly, the present invention features a process for the hydroxylation of phenols or phenol ethers of the general formula (1):

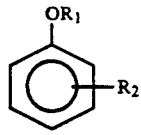

in which $R_1$ is a hydrogen atom, or a methyl, ethyl or phenyl radical, and $R_2$ is a hydrogen atom, an alkyl radical having from 1 to 4 carbon atoms, an alkoxy radical having from 1 to 4 carbon atoms, or a phenyl or cyclohexyl radical, comprising reacting such phenol/-phenol ether with hydrogen peroxide, in the presence of (a) a catalytically effective amount of an alkali metal or alkaline earth metal salt of at least one protonic acid having a pKa in water of less than −0.1, and (b) an effective amount of at least one phosphorus oxyacid.

DETAILED DESCRIPTION OF THE PREFERRED EMBODIMENTS OF THE INVENTION

More particularly according to the present invention, the protonic acids, the salts of which serve as catalysts in the subject process, are preferably those having a pKa in water of less than −1.

By "pKa" is intended the ionic dissociation constant of the acid/base system when water is used as the solvent.

Exemplary of the salts of such acids having the above definition, preferred are the alkali metal or alkaline earth metal salts of acids which are stable to oxidation by hydrogen peroxide.

Thus, particularly representative such salts include the alkali metal or alkaline earth metal salts of sulfuric acid, pyrosulfuric acid, perchloric acid, nitric acid, halogenosulfonic acids such as chlorosulfonic acid and fluorosulfonic acid, trifluoromethanesulfonic acid, methanesulfonic acid, ethanesulfonic acid, ethanedisulfonic acid, benzenesulfonic acid, the benzenedisulfonic acids, the toluenesulfonic acids, the naphthalenesulfonic acids and the naphthalenedisulfonic acids.

By "alkali metal salts" are intended the neutral lithium, sodium, potassium, rubidium and cesium salts of the acids described above.

More preferred are the sodium or potassium salts, and even more preferably, for economic reasons, the sodium salts.

Among these various salts, those preferred are disodium sulfate, sodium perchlorate, sodium trifluoromethanesulfonate, sodium paratoluenesulfonate, sodium chlorosulfonate, sodium fluorosulfonate and sodium methanesulfonate.

By "alkaline earth metal salts" are intended the neutral beryllium, magnesium, calcium, strontium and barium salts of the acids described above.

Preferred are the magnesium, calcium and barium salts.

Among these various alkaline earth metal salts, those preferred are calcium sulfate, magnesium sulfate, calcium perchlorate, magnesium perchlorate, calcium trifluoromethanesulfonae, magnesium trifluoromethanesulfonate, calcium paratoluenesulfonate, magnesium paratoluenesulfonate, calcium fluorosulfonate, magnesium fluorosulfonate, calcium methanesulfonate and magnesium methanesulfonate.

Mixtures of several alkali metal or alkaline earth metal salts may likewise be used.

The alkali metal or alkaline earth metal salts may also be prepared in situ, for example by charging stoichiometric amounts of acid and oxide or hydroxide of these metals.

The phosphorus oxyacids are more particularly the compounds of phosphorus having a degree of oxidation of 5 which have an acid function.

Compounds of phosphorus having a degree of oxidation of 3 which have an acid function, and which will be oxidized in the mixture by hydrogen peroxide to corresponding compounds of phosphorus V, may also be used; however, this is of no particular value, while presenting the drawback of consuming a certain amount of the hydrogen peroxide.

Exemplary of such oxyacids of phosphorus V are orthophosphoric acid, metaphosphoric acid, pyrophosphoric acid, polyphosphoric acids and phosphonic acids, such as 1-hydroxyethylidenediphosphonic acid, phosphonic acid, ethylphosphonic aid and phenylphosphonic acid.

For practical and economic reasons, those preferably used are orthophosphoric acid, pyrophosphoric acid and 1-hydroxyethylidenediphosphonic acid.

The amount of alkali metal or alkaline earth metal salt used in the process of the invention can vary over wide limits.

Generally, this amount is expressed as the molar ratio of alkali metal or alkaline earth metal salt/hydrogen peroxide. This ratio advantageously ranges from 0.1 mole % to 10 mole % and preferably from 0.5% to 5%.

The amount of phosphorus oxyacid, expressed as the molar ratio of phosphorus oxyacid/hydrogen peroxide, advantageously ranges from 0.1 mole % to 20 mole % and preferably from 0.5% to 10%.

The hydrogen peroxide can be used in the form of an aqueous solution, or of an organic solution.

As the aqueous solutions are more readily available commercially, these are preferably used. Generally they contain more than 20% by weight of hydrogen peroxide.

The amount of hydrogen peroxide can be up to 1 mole of $H_2O_2$ per 1 mole of phenolic compound of formula (I).

However, it is preferable, in order to obtain industrially acceptable yields, to use a molar ratio of phenolic compound of formula (I)/hydrogen peroxide of 25/1 to 3/1 and preferably of 2o/1 to 4/1.

In order to provide a sufficient reaction rate, the initial water content of the medium is limited to 20% by weight and preferably to 10% by weight. This initial water corresponds to the water introduced with the reactants and in particular with the hydrogen peroxide.

Representative phenolic compounds of formula (I) which can be used in the process of the invention are phenol, anisole, orthocresol, paracresol, metacresol, 4-tert-butylphenol, 2-methoxyphenol and 4-methoxyphenol.

The present process is very particularly suitable for the preparation of hydroquinone and of pyrocatechol from phenol.

The temperature at which the hydroxylation reaction is carried out typically ranges from 45° C. to 160° C. under atmospheric pressure.

The reaction can also be conducted at higher temperatures and under a pressure greater than atmospheric pressure.

The reactants and the operating conditions are well adapted for continuously carrying out the process of the invention.

In order to further illustrate the present invention and the advantages thereof, the following specific examples are given, it being understood that same are intended only as illustrative and in nowise limitative.

EXAMPLE 1

The following materials were charged into a 100 cm³ glass round-bottomed flask fitted with an ascending condenser, a thermometer, a discharge funnel and a central stirrer:

(i) 47 g (0.5 mole) of phenol;
(ii) 0.137 g (0.615 mmole) of Mg($ClO_4$)$_2$: 1.23 mole % relative to hydrogen peroxide; and
(iii) 0.053 g (0.3 mmole) of pyrophosphoric acid: 0.6 mole % relative to hydrogen peroxide.

After increasing the temperature of the above mixture to 75 C with stirring, 2.44 g of a 69.5 % weight/weight aqueous solution of hydrogen peroxide (0.05 mole) were introduced.

After heating at 75° C. for 3 hours, the residual hydrogen peroxide was determined by iodometry and the diphenols formed were determined by high performance liquid chromatography.

| | |
|---|---|
| (a) Degree of conversion (DC) of $H_2O_2$: | 100% |
| (b) Yield of hydroquinone relative to $H_2O_2$ converted: | 28.5% |
| (c) Yield of pyrocatechol relative to $H_2O_2$ converted: | 42.0% |
| (d) Total yield of diphenols: | 70.5% |

EXAMPLE 2

The following materials were charged into a 100 cm³ glass round-bottomed flask fitted with an ascending condenser, a thermometer, a discharge funnel and a central stirrer:

(i) 47 g (0.5 mole) of phenol;
(ii) 0.271 g (1.215 mmole) of Mg($ClO_4$)$_2$: 2.43 mole % relative to hydrogen peroxide; and
(iii) 0.107 g (0.6 mmole) of pyrophosphoric acid: 1.2 mole % relative to hydrogen peroxide.

After heating the above mixture to 75° C. with stirring, 2.44 g of a 69.5 % weight/weight aqueous solution of hydrogen peroxide (0.05 mole) were introduced.

After heating at 75° C. for 2 hours, 20 minutes, the residual hydrogen peroxide was determined by iodometry and the diphenols formed were determined by high performance liquid chromatography.

| | |
|---|---|
| (a) Degree of conversion (DC) of $H_2O_2$: | 100%; |
| (b) Yield of hydroquinone relative to $H_2O_2$ converted (YLD): | 29.9%; |
| (c) Yield of pyrocatechol relative to $H_2O_2$ converted (YLD): | 42.0%; |
| (d) Total yield of diphenols: | 71.0%. |

EXAMPLE 3

The procedure of Example 1 was repeated, but replacing pyrophosphoric acid by 0.45 mmole of orthophosphoric acid (0.9 mole % relative to hydrogen peroxide).

After reaction at 75° C. for 5 hours, 25 minutes, the following results were obtained:

| | |
|---|---|
| (a) DC of $H_2O_2$: | 97.0%; |
| (b) YLD of hydroquinone: | 23.0%; |
| (c) YLD of pyrocatechol: | 36.0%; |
| (d) Total YLD of diphenols: | 59.0%. |

EXAMPLE 4

The procedure of Example 1 was repeated, but replacing pyrophosphoric acid by 0.3 mmole of 1-hydroxyethylidenediphosphonic acid (0.6 mole % relative to hydrogen peroxide).

After reaction at 75° C. for 3 hours, 25 minutes, the following results were obtained:

| | |
|---|---|
| (a) DC of $H_2O_2$: | 100%; |
| (b) YLD of hydroquinone: | 30.0%; |
| (c) YLD of pyrocatechol: | 41.5%; |
| (d) Total YLD of diphenols: | 71.5%. |

COMPARATIVE EXPERIMENT A

The procedure of Example 1 was repeated, but omitting the magnesium salt.

After reaction at 75° C. for 5 hours, 15 minutes, the following results were obtained:

| (a) DC of $H_2O_2$: | 16.5%; |
|---|---|
| (b) YLD of hydroquinone: | 16.5%; |
| (c) YLD of pyrocatechol: | 38.5%; |
| (d) Total YLD of diphenols: | 55.0%. |

In the absence of an alkali metal or alkaline earth metal salt, a very low degree of conversion of $H_2O_2$ was observed, despite a longer reaction time than in Example 1.

COMPARATIVE EXPERIMENT B

The procedure of Example 2 was repeated, but omitting the pyrophosphoric acid.

After reaction at 75° C. for 4 hours, 25 minutes, the following results were obtained:

| (a) DC of $H_2O_2$: | 52.5%; |
|---|---|
| (b) YLD of hydroquinone: | 13.5%; |
| (c) YLD of pyrocatechol: | 29.5%; |
| (d) Total YLD of diphenols: | 43.0%. |

In the absence of phosphorus oxyacid, a lower degree of conversion of $H_2O_2$, despite a longer reaction time, and a lower yield of diphenols than in Example 2, were observed.

COMPARATIVE EXPERIMENT C

The procedure of Example 2 was repeated, but omitting the magnesium salt.

The amount of 69.5% weight/weight hydrogen peroxide charged was 1.31 g (26.8 mmole): the molar ratio of phenol/$H_2O_2$ was therefore 18.6.

After reaction at 150° C. for 2 hours, the following results were obtained:

| (a) DC of $H_2O_2$: | 99.5%; |
|---|---|
| (b) YLD of hydroquinone: | 19.5%; |
| (c) YLD of pyrocatechol: | 35.0%; |
| (d) Total YLD of diphenols: | 54.5%. |

In the absence of alkali metal or alkaline earth metal salt, it was observed that it was necessary to operate at a very much higher temperature to obtain a degree of conversion of $H_2O_2$ equivalent to that of Example 2 (while the initial $H_2O_2$/phenol ratio was higher), while having a lower yield of diphenols.

COMPARATIVE EXPERIMENT D

The following materials were charged into a 100 cm$^3$ glass round-bottomed flask fitted with an ascending condenser, a thermometer, a discharge funnel and a central stirrer:

(i) 51.5 g (0.548 mole) of phenol;
(ii) 0.0981 g (0.68 mmole) of $HClO_4$: 1.23 mole % relative to hydrogen peroxide; and
(iii) 0.058 g (0.33 mmole) of pyrophosphoric acid: 0.6 mole % relative to hydrogen peroxide.

After heating this mixture to 75° C. with stirring, 2.70 g of a 69.5% weight/weight aqueous solution of hydrogen peroxide (55.2 mmole) were introduced.

After heating at 75° C. for 2 hours, the residual hydrogen peroxide was determined by iodometry and the diphenols formed were determined by high performance liquid chromatography.

| (a) Degree of conversion (DC) of $H_2O_2$: | 99.5; |
|---|---|
| (b) Yield of hydroquinone relative to $H_2O_2$ converted: | 30.0%; |
| (c) Yield of pyrocatechol relative to $H_2O_2$ converted: | 42.0%; |
| (d) Total yield of diphenols: | 72.0%. |

COMPARATIVE EXPERIMENT E

The following materials were charged into a 100 cm$^3$ glass round-bottomed flask fitted with an ascending condenser, a thermometer, a discharge funnel and a central stirrer:

(i) 58.1 g (0.618 mole) of phenol;
(ii) 0.222 g (1.58 mmole) of Mg acetate: 2.53 mole % relative to hydrogen peroxide; and
(iii) 0.074 g (0.42 mmole) of pyrophosphoric acid:, 0.67 mole % relative to hydrogen peroxide.

After heating this mixture to 75° C. with stirring, 3.05 g of a 69.5% weight/weight aqueous solution of hydrogen peroxide (62.4 mmole) were introduced.

After heating at 75° C. for 2 hours, 10 minutes, the residual hydrogen peroxide was determined by iodometry and the diphenols formed were determined by high performance liquid chromatography.

The following results were obtained:

| (a) Degree of conversion (DC) of $H_2O_2$: | 7.5; |
|---|---|
| (b) Yield of hydroquinone relative to $H_2O_2$ converted: | 8.0%; |
| (c) Yield of pyrocatechol relative to $H_2O_2$ converted: | 15.0%; |
| (d) Total yield of diphenols: | 23.0%. |

EXAMPLE 5 TO 11

The following materials were charged into the apparatus described in Example 1:

(i) 47.0 g (0.5 mole) of phenol;
(ii) $NaClO_4.H_2O$: mole % relative to hydrogen peroxide reported in the Table;
(iii) pyrophosphoric acid: mole % relative to hydrogen peroxide reported in the Table.

After heating this mixture to 75° C. or 100° C. with stirring, variable amounts of a 69.5% weight/weight aqueous solution of hydrogen peroxide were introduced (see $H_2O_2$/phenol molar ratios in the Table).

After variable heating times at 75° C. or 100° C. (see Table), the results reported in the following Table were obtained.

The following abbreviations have been used:
DC%=degree of conversion %;
YLD HQ=yield of hydroquinone relative to $H_2O_2$ converted;
YLD PC=yield of pyrocatechol relative to $H_2O_2$ converted;
YLD total=total yield of diphenols.

TABLE

| $H_2O_2$/phenol | $NaClO_4/H_2O_2$ | $H_4P_2O_7/H_2O_2$ |

TABLE-continued

| Examples | (mole %) | (mole %) | (mole %) |
|---|---|---|---|
| Ex. 5 | 5.7 | 2.34 | 1.1 |
| Ex. 6 | 5.3 | 2.35 | 5.3 |
| Ex. 7 | 10.1 | 3.6 | 0.7 |
| Ex. 8 | 10.0 | 1.26 | 2.7 |
| Ex. 9 | 10.4 | 1.75 | 5.1 |
| Ex. 10 | 5.45 | 1.15 | 2.61 |
| Ex. 11 | 5.13 | 1.27 | 2.66 |

| T °C. | Time | DC % $H_2O_2$ | YLD % HQ | YLD % PC | YLD % total |
|---|---|---|---|---|---|
| 100 | 4 h | 100 | 27.0 | 42.5 | 69.5 |
| 75 | 4 h, 15 min | 98.5 | 33.5 | 50.5 | 84.0 |
| 75 | 5 h, 30 min | 77.0 | 27.0 | 41.0 | 68.0 |
| 75 | 7 h | 92.0 | 28.0 | 43.5 | 71.5 |
| 75 | 6 h | 100 | 27.0 | 41.5 | 68.5 |
| 75 | 6 h | 97.0 | 34.0 | 47.0 | 81.0 |
| 100 | 4 h | 99.0 | 33.0 | 49.0 | 82.0 |

EXAMPLE 12 AND COMPARATIVE EXPERIMENT F

EXAMPLE 12

The following materials were charged into the apparatus described in Example 1:

(i) 42.9 g (0.456 mole) of phenol;
(ii) 0.285 g (1.16 mmole) of $MgSO_4.7H_2O$: 2.56 mole % relative to hydrogen peroxide; and
(iii) 0.0746 g (0.42 mmole) of pyrophosphoric acid: 0.93 mole % relative to hydrogen peroxide.

After heating this mixture to 75° C. with stirring, 2.21 g of a 69.5% weight/weight aqueous solution of hydrogen peroxide (45.2 mmole) were introduced.

After reaction at 75° C. for 6 hours, the following results were obtained:

| (a) DC of $H_2O_2$: | 73.0%; |
|---|---|
| (b) YLD of hydroquinone: | 23.5%; |
| (c) YLD of pyrocatechol: | 46.5%; |
| (d) Total YLD of diphenols: | 70.0%. |

COMPARATIVE EXPERIMENT F

The procedure of Example 12 was repeated in the absence of pyrophosphoric acid.

The following results were obtained:

| (a) DC of $H_2O_2$: | 6.3%; |
|---|---|
| (b) YLD of hydroquinone: | 15.9%; |
| (c) YLD of pyrocatechol: | 28.8%; |
| (d) Total YLD of diphenols: | 44.7%. |

In the absence of phosphorus oxyacid, a very low degree of conversion of $H_2O_2$ and also a yield of diphenols which was lower than in Example 12, were observed.

EXAMPLE 13

The following materials were charged into the apparatus described in Example 1:

(i) 44.5 g (0.473 mole) of phenol;
(ii) 0.153 g (1.12 mmole) of $CaSO_4$: 2.28 mole % relative to hydrogen peroxide;
(iii) 0.0517 g (0.29 mmole) of pyrophosphoric acid: 0.6 mole % relative to hydrogen peroxide.

After heating this mixture to 75° C. with stirring, of a 69.5% weight/weight aqueous solution of hydrogen peroxide (49 mmole) were introduced.

After reaction at 75° C. for 4 hours, 30 minutes, the following results were obtained:

| (a) DC of $H_2O_2$: | 23.0%; |
|---|---|
| (b) YLD of hydroquinone: | 21.0%; |
| (c) YLD of pyrocatechol: | 40.0%; |
| (d) Total YLD of diphenols: | 61.0%. |

EXAMPLE 14

The following materials were charged into the apparatus described in Example 1:

(i) 39.4 g (0.418 mole) of phenol;
(ii) 0.086 g (0.55 mmole) of lithium trifluorosulphonate: 1.23 mole % relative to hydrogen peroxide;
(iii) 0.047 g (0.26 mmole) of pyrophosphoric acid: 0.6 mole % relative to hydrogen peroxide.

After heating this mixture to 75° C. with stirring, 2.07 g of a 69.5% weight/weight aqueous solution of hydrogen peroxide (42.3 mmole) were introduced.

After reaction at 75° C. for 6 hours, the following results were obtained:

| (a) DC of $H_2O_2$: | 81.5%; |
|---|---|
| (b) YLD of hydroquinone: | 26.0%; |
| (c) YLD of pyrocatechol: | 41.5%; |
| (d) Total YLD of diphenols: | 67.5%. |

EXAMPLE 15

The following materials were charged into a 30 cm³ reactor fitted with an ascending condenser connected to a gasometer, a thermometer, a controlled heating system, an injection system and a central bar magnet stirrer:

(i) 9.4 g (0.1 mole) of phenol;
(ii) 0.137 g (0.615 mmole) of $Cs_2SO_4$: 2.5 mole % relative to hydrogen peroxide;
(iii) 0.011 g (0.06 mmole) of pyrophosphoric acid: 0.6 mole % relative to hydrogen peroxide.

After heating this mixture to 75° C. with stirring, 0.49 g of a 69.5% weight/weight aqueous solution of hydrogen peroxide (10 mmole) were introduced.

After reaction at 75° C. for 4 hours, the following results were obtained:

| (a) Yield of hydroquinone relative to $H_2O_2$ charged: | 16.5%; |
|---|---|
| (b) Yield of pyrocatechol relative to $H_2O_2$ charged: | 39.5%; |
| (c) Total yield of diphenols: | 56.0%. |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the hydroxylation of a phenol or phenol ether of the general formula (I):

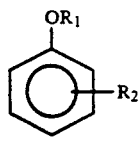 (I)

in which $R_1$ is a hydrogen atom, or a methyl, ethyl or phenyl radical, and $R_2$ is a hydrogen atom, an alkyl radical having from 1 to 4 carbon atoms, an alkoxy radical having from 1 to 4 carbon atoms, or a phenyl or cyclohexyl radical, comprising reacting such phenol/phenol ether with hydrogen peroxide, in the presence of (a) a catalytically effective amount of an alkali metal or alkaline earth metal salt of at least one protonic acid having a pKa in water of less than $-0.1$, and (b) an effective amount of at least one phosphorus oxyacid so as to produce a hydroxylated product.

2. The process as defined by claim 1 said at least one protonic acid having a pKa in water of less than $-1$.

3. The process as defined by claim 1, said alkali metal or alkaline earth metal salt comprising a salt of sulfuric acid, pyrosulfuric acid, perchloric acid, nitric acid, halogenosulfonic acid, trifluoromethanesulfonic acid, methanesulfonic acid, ethanesulfonic acid, ethanedisulfonic acid, benzenesulfonic acid, a benzenedisulfonic acid, a toluenesulfonic acid, a naphthalenesulfonic acid, or a naphthalenedisulfonic acid.

4. The process as defined by claim 3, carried out in the presence of a neutral lithium, sodium, potassium, rubidium or cesium salt of such acids.

5. The process as defined by claim 4, carried out in the presence of disodium sulfate, sodium perchlorate, sodium trifluoromethanesulfonate, sodium paratoluenesulfonate, sodium chlorosulfonate, sodium fluorosulfonate or sodium methanesulfonate.

6. The process as defined by claim 3, carried out in the presence of a neutral beryllium, magnesium, calcium strontium or barium salt of such acids.

7. The process as defined by claim 6, carried out in the presence of calcium sulfate, magnesium sulfate, calcium perchlorate, magnesium perchlorate, calcium trifluoromethanesulfonate, magnesium trifluoromethanesulfonate, calcium paratoluenesulfonate, magnesium paratoluenesulfonate, calcium fluorosulfonate, magnesium fluorosulfonate, calcium methanesulfonate or magnesium methanesulfonate.

8. The process as defined by claim 1, carried out in the presence of a mixture of at least two alkali metal or alkaline earth metal salts.

9. The process as defined by claim 1, said at least one phosphorus oxyacid having a degree of oxidation of 5 and comprising an acid function.

10. The process as defined by claim 9, said oxyacid of phosphorus V comprising orthophosphoric acid, metaphosphoric acid, pyrophosphoric acid, a polyphosphoric acid or a phosphonic acid.

11. The process as defined by claim 10, said phosphorus oxyacid comprising orthophosphoric acid, pyrophosphoric acid or 1-hydroxyethylidenediphosphonic acid.

12. The process as defined by claim 1, wherein the amount of alkali metal or alkaline earth metal salt, expressed as the molar ratio of alkali metal or alkaline earth metal salt/hydrogen peroxide, ranges from 0.1% to 10%.

13. The process as defined by claim 1, wherein the amount of phosphorus oxyacid, expressed as the molar ratio of phosphorus oxyacid/hydrogen peroxide, ranges from 0.1% to 20%.

14. The process as defined by claim 1, wherein the molar ratio of phenolic compound of formula (I)/hydrogen peroxide ranges from 25/1 to 3/1.

15. The process as defined by claim 1, said phenolic compound of formula (I) comprising phenol, anisole, orthocresol, paracresol, metacresol, 4-tert-butylphenol, 2-methoxyphenol and 4-methoxyphenol.

16. The process as defined by claim 4, carried out in the presence of a sodium or potassium salt.

17. The process as defined by claim 6, carried out in the presence of a calcium, magnesium or barium salt.

18. The process as defined by claim 12, said molar ratio ranging from 0.5% to 5%.

19. The process as defined by claim 13, said molar ratio ranging from 0.5% to 10%.

20. The process as defined by claim 14, said molar ratio ranging from 20/1 to 4/1.

21. The process as defined by claim 15, said phenolic compound of formula (I) comprising phenol.

22. The process as defined by claim 1, said hydrogen peroxide comprising an aqueous solution thereof.

23. The process as defined by claim 1, carried out continuously.

* * * * *